(12) United States Patent
Bianchetti et al.

(10) Patent No.: US 11,111,459 B2
(45) Date of Patent: Sep. 7, 2021

(54) LAUNDRY DETERGENT COMPOSITIONS WITH STAIN REMOVAL

(71) Applicant: The Procter & Gamble Company, Cincinnati, OH (US)

(72) Inventors: Giulia Ottavia Bianchetti, Brussels (BE); Neil Joseph Lant, Newcastle upon Tyne (GB); Steven George Patterson, Washington Tyne & Wear (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/831,866

(22) Filed: Mar. 27, 2020

(65) Prior Publication Data
US 2020/0308507 A1 Oct. 1, 2020

(30) Foreign Application Priority Data
Mar. 29, 2019 (EP) ..................................... 19166201

(51) Int. Cl.
| | | |
|---|---|---|
| *C12N 9/88* | (2006.01) | |
| *C11D 1/83* | (2006.01) | |
| *C11D 1/14* | (2006.01) | |
| *C11D 1/22* | (2006.01) | |
| *C11D 1/29* | (2006.01) | |
| *C11D 1/72* | (2006.01) | |
| *C11D 3/386* | (2006.01) | |
| *C11D 11/00* | (2006.01) | |
| *C12N 9/24* | (2006.01) | |

(52) U.S. Cl.
CPC ................ *C11D 1/83* (2013.01); *C11D 1/143* (2013.01); *C11D 1/146* (2013.01); *C11D 1/22* (2013.01); *C11D 1/29* (2013.01); *C11D 1/72* (2013.01); *C11D 3/38636* (2013.01); *C11D 11/0017* (2013.01); *C12N 9/2405* (2013.01); *C12N 9/2488* (2013.01); *C12Y 402/02012* (2013.01)

(58) Field of Classification Search
CPC .......................... C12N 9/88; C12Y 402/02012
See application file for complete search history.

(56) References Cited

U.S. PATENT DOCUMENTS

2020/0040320 A1   2/2020   Spodsberg

FOREIGN PATENT DOCUMENTS

| WO | WO0042146 A1 | 7/2000 |
| WO | WO2019038059 A1 | 2/2019 |

OTHER PUBLICATIONS

PCT Search Report for appl. No. PCT/US2020/024591, dated Jun. 16, 2020, 9 pages.
EP Search report for appl. No. 19166201.4-1105, dated Sep. 18, 2019, 6 pages.

*Primary Examiner* — Tekchand Saidha
(74) *Attorney, Agent, or Firm* — Andrés E. Velarde

(57) ABSTRACT

The need for a laundry detergent composition which provides improved removal of stains comprising a combination of mannans and other polysaccharides, is met using a combination of detersive surfactant and a cocktail of enzymes comprising a xanthan endoglucanase, a xanthan lyase, and a mannanase.

20 Claims, No Drawings
Specification includes a Sequence Listing.

LAUNDRY DETERGENT COMPOSITIONS WITH STAIN REMOVAL

FIELD OF THE INVENTION

Laundry detergent compositions, especially liquid laundry detergent compositions for cleaning mixed food stains.

BACKGROUND OF THE INVENTION

Laundry detergent compositions are formulated to provide good cleaning to fabrics: To keep white fabrics white, and to keep coloured fabrics bright. The laundry detergent compositions are also typically formulated to remove stains. A stain is a local discoloration that can be clearly distinguished on the fabric it is found upon. Since they result in a discoloration that strongly contrasts with the unstained fabrics, they are particularly noticeable on fabrics.

Certain mixed food stains, such as prepared sauces, remain challenging to remove, especially at low temperatures. Moreover, such stains have been found to redeposit on the fabric during laundering, despite the use of anti-redeposition aids. While improved removal of such stains can be achieved by increasing the levels of actives such as anti-redeposition aids, surfactants, and builders, this adds to the cost of the formulation and can lead to other issues such as stability.

Hence, a need remains for a laundry detergent composition which has improved efficacy against mixed food stains, such as prepared sauces, while being stable and without the need for high levels of stain treatment actives.

WO2019/038059 relates to detergent compositions comprising endoglucanase variants and methods for use of said compositions. WO2019/038060 relates to detergent compositions comprising xanthan lyase variants and methods for use of said compositions.

SUMMARY OF THE INVENTION

The present invention relates to a laundry detergent composition comprising: detersive surfactant, wherein the detersive surfactant comprises a combination of anionic and nonionic surfactant; an enzyme system comprising: a xanthan endoglucanase, wherein said xanthan endoglucanase comprises a polypeptide with at least 60% sequence identity to SEQ ID NO: 1; a xanthan lyase, wherein said xanthan lyase comprises a polypeptide with at least 60% sequence identity to SEQ ID NO: 2, and a mannanase, wherein said mannanase comprises a polypeptide with at least 85% sequence identity to residues 27-331 of SEQ ID NO: 3 and/or at least 80% sequence identity to SEQ ID NO: 4.

The present invention further relates to a method of laundering fabric, preferably a fabric comprising a stain wherein the stain comprises a combination of mannans and polysaccharides, wherein the method comprises the steps of: providing a laundry detergent composition of the invention; diluting the laundry detergent composition to provide a wash liquor having a total surfactant concentration of greater than 300 ppm; and washing fabric in the wash liquor.

DETAILED DESCRIPTION OF THE INVENTION

It has surprisingly been found that the resiliency of certain mixed food stains, such as certain prepared sauces, is due to the combination of mannans and other polysaccharides. Such sauces can include chilli pastes, vinegar dressings, and some ice-creams. Examples of such mannans include locust bean, tara gum, guar gum, and the like, as well as mixtures thereof. Examples of polysaccharides include xanthan gum. It is believed that the combination of mannans and polysaccharides forms gels as the soil dries, resulting in hard to remove stains. In addition, the resiliency of such gels can be increased in the presence of greasy or oily residues such as animal fats (e.g. bacon grease, lard, shortening, butter) and vegetable oils (e.g. sunflower oil, rapeseed oil, cottonseed oil, olive oil, corn oil). In addition, even if the stain is removed, the gel-like structure results in the stains holding together in suspension during the wash cycle, resulting in greater redeposition. It is believed that the enzyme system of use in the present invention is better able to break down these gel structures, more effectively than mannanase alone or endoglucanases alone, even when the gel structures comprise greasy or oily residues, and hence results in improved removal of such stains. In addition, since the enzyme system is better able to break down such gel structures, reduced redeposition of the soils is also achieved.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

All measurements are performed at 25° C. unless otherwise specified.

As used herein, the articles including "a" and "an" when used in a claim, are understood to mean one or more of what is claimed or described.

Laundry Detergent Composition:

The laundry detergent composition can be in any suitable form, such as liquid, paste, granular, solid, powder, or in conjunction with a carrier such as a substrate. Preferred laundry detergent compositions are either liquid or granular, with liquid being most preferred.

As used herein, "liquid detergent composition" refers to liquid detergent composition which is fluid, and preferably capable of wetting and cleaning a fabric, e.g., clothing in a domestic washing machine. As used herein, "laundry detergent composition" refers to compositions suitable for washing clothes. The composition can include solids or gases in suitably subdivided form, but the overall composition excludes product forms which are non-fluid overall, such as tablets or granules. The liquid laundry detergent composition preferably has a density in the range from 0.9 to 1.3 grams per cubic centimeter, more specifically from 1.00 to 1.10 grams per cubic centimeter, excluding any solid additives but including any bubbles, if present.

Aqueous liquid laundry detergent compositions are preferred. For such aqueous liquid laundry detergent compositions, the water content can be present at a level of from 5% to 99%, preferably from 15% to 90%, more preferably from 25% to 80% by weight of the liquid detergent composition.

The pH range of the detergent composition is from 6.0 to 8.9, preferably from pH 7 to 8.8. The detergent composition can also be encapsulated in a water soluble film, to form a unit dose article. Such unit dose articles comprise a detergent composition of the present invention, wherein the detergent composition comprises less than 20%, preferably less than 15%, more preferably less than 10% by weight of water, and the detergent composition is enclosed in a water-soluble or dispersible film. Such unit-dose articles can be formed using any means known in the art.

Suitable water soluble pouch materials include polymers, copolymers or derivatives thereof. Preferred polymers, copolymers or derivatives thereof can be selected from the group consisting of: polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof.

Detersive Surfactants

Detersive surfactant as used herein means surfactants or mixtures of surfactants that provide cleaning, stain removing, or laundering benefit to soiled material. Suitable detersive surfactants can be: anionic surfactant, nonionic surfactant, zwitterionic surfactant, and combinations thereof. The detersive surfactant comprises a combination of anionic and nonionic surfactant.

The laundry composition can comprises detersive surfactant at a level of from 3 wt % to 50 wt %, preferably from 10 wt % to 37.5 wt %, more preferably from 15 wt % to 30 wt %.

Suitable anionic surfactants can be selected from the group consisting of: alkyl sulphates, alkyl ethoxy sulphates, alkyl sulphonates, alkyl benzene sulphonates, fatty acids and their salts, and mixtures thereof. However, by nature, every anionic surfactant known in the art of detergent compositions may be used, such as disclosed in "Surfactant Science Series", Vol. 7, edited by W. M. Linfield, Marcel Dekker. However, the composition preferably comprises at least a sulphonic acid surfactant, such as a linear alkyl benzene sulphonic acid, but water-soluble salt forms may also be used. Alkyl ethoxy sulphates, or mixtures thereof, are also preferred.

Anionic sulfonate or sulfonic acid surfactants suitable for use herein include the acid and salt forms of linear or branched alkylbenzene sulfonates, alkyl ester sulfonates, alkane sulfonates, alkyl sulfonated polycarboxylic acids, and mixtures thereof. Suitable anionic sulfonate or sulfonic acid surfactants include: C5-C20 alkylbenzene sulfonates, more preferably C10-C16 alkylbenzene sulfonates, more preferably C11-C13 alkylbenzene sulfonates, C5-C20 alkyl ester sulfonates, C6-C22 primary or secondary alkane sulfonates, C5-C20 sulfonated polycarboxylic acids, and any mixtures thereof, but preferably C11-C13 alkylbenzene sulfonates. The aforementioned surfactants can vary widely in their 2-phenyl isomer content. Such sulfonate or sulfonic acid surfactants can be present at a level of from 1.0% to 20%, more preferably from 5.0% to 15%, and most preferably from 6.5 to 12.5% by weight of the composition.

Anionic sulphate salts suitable for use in the compositions of the invention include the primary and secondary alkyl sulphates, having a linear or branched alkyl or alkenyl moiety having from 9 to 22 carbon atoms or more preferably 12 to 18 carbon atoms. Also useful are beta-branched alkyl sulphate surfactants or mixtures of commercial available materials, having a weight average (of the surfactant or the mixture) branching degree of at least 50%.

Other suitable anionic surfactants for use herein include fatty methyl ester sulphonates and/or alkyl alkoxylated sulphates such as alkyl ethoxy sulphates (AES) and/or alkyl polyalkoxylated carboxylates (AEC). When used, the alkyl alkoxylated sulphate surfactant is preferably a blend of one or more alkyl ethoxylated sulphates. Suitable alkyl alkoxylated sulphates include C10-C18 alkyl ethoxylate, more preferably C12-C15 alkyl ethoxylate, with a degree of ethoxylation of from 1 to 5, preferably from 2 to 3. Such alkyl alkoxylated sulphates are preferably present at a level of from 1.0% to 10%, more preferably from 2.0% to 7.5%, and most preferably from 3.0 to 5% by weight of the composition.

Suitable fatty acids include "natural" fatty acids, for example coconut, palm kernel, olive oil or tallow fatty acid and mixtures thereof. Such fatty acid surfactants can be present at a level of from 1.0% to 15%, more preferably from 2.0% to 12.5%, and most preferably from 5.0 to 10% by weight of the composition.

The anionic surfactants are typically present in the form of their salts with alkanolamines or alkali metals such as sodium and potassium.

The liquid detergent composition can comprise nonionic surfactant. The level of nonionic surfactant in the liquid detergent composition can be present at a level of from 1.0% to 20%, preferably from 2.5% to 15%, more preferably from 5.0% to 12.5% by weight of the composition.

Suitable nonionic surfactants include, but are not limited to C12-C18 alkyl ethoxylates ("AE") including the so-called narrow peaked alkyl ethoxylates and C6-C12 alkyl phenol alkoxylates (especially ethoxylates and mixed ethoxy/propoxy), block alkylene oxide condensate of C6-C12 alkyl phenols, alkylene oxide condensates of C8-C22 alkanols and ethylene oxide/propylene oxide block polymers (Pluronic-BASF Corp.), as well as semi polar nonionics (e.g., amine oxides and phosphine oxides) can be used in the present compositions. An extensive disclosure of these types of surfactants is found in U.S. Pat. No. 3,929,678, Laughlin et al., issued Dec. 30, 1975.

Alkylpolysaccharides such as disclosed in U.S. Pat. No. 4,565,647 Llenado are also useful nonionic surfactants in the compositions of the invention.

Also suitable are alkyl polyglucoside surfactants.

Nonionic surfactants of use include those of the formula $R_1(OC_2H_4)_nOH$, wherein $R_1$ is a C10-C16 alkyl group or a C8-C12 alkyl phenyl group, and n is from preferably 3 to 80. In some embodiments, the nonionic surfactants may be condensation products of C12-C15 alcohols with from 5 to 20 moles of ethylene oxide per mole of alcohol, e.g., C12-C13 alcohol condensed with 6.5 moles of ethylene oxide per mole of alcohol Suitable amine oxide surfactants are amine oxides having the following formula: $R_1R_2R_3NO$ wherein $R_1$ is an hydrocarbon chain comprising from 1 to 30 carbon atoms, preferably from 6 to 20, more preferably from 8 to 16 and wherein $R_2$ and $R_3$ are independently saturated or unsaturated, substituted or unsubstituted, linear or branched hydrocarbon chains comprising from 1 to 4 carbon atoms, preferably from 1 to 3 carbon atoms, and more preferably are methyl groups. $R_1$ may be a saturated or unsaturated, substituted or unsubstituted linear or branched hydrocarbon chain.

Suitable amine oxides for use herein are for instance preferably $C_{12}$-$C_{14}$ dimethyl amine oxide, commercially available from Albright & Wilson, $C_{12}$-$C_{14}$ amine oxides commercially available under the trade name Genaminox® LA from Clariant or AROMOX® DMC from AKZO Nobel. Additional suitable nonionic surfactants include polyhydroxy fatty acid amides of the formula:

wherein R is a C9-17 alkyl or alkenyl, R1 is a methyl group and Z is glycidyl derived from a reduced sugar or alkoxylated derivative thereof. Examples are N-methyl N-1-deoxyglucityl cocoamide and N-methyl N-1-deoxyglucityl oleamide. Processes for making polyhydroxy fatty acid amides are known and can be found in Wilson, U.S. Pat. No. 2,965,576 and Schwartz, U.S. Pat. No. 2,703,798.

The liquid detergent composition can comprise a zwitterion. The zwitterion can be present at a level of from 0.1 wt % to 5 wt %, preferably from 0.2 wt % to 2 wt %, more preferably from 0.4 wt % to 1 wt %.

Suitable amphoteric or zwitterionic detersive surfactants include those which are known for use in hair care or other personal care cleansing. Non-limiting examples of suitable zwitterionic or amphoteric surfactants are described in U.S. Pat. No. 5,104,646 (Bolich Jr. et al.), U.S. Pat. No. 5,106,609 (Bolich Jr. et al.). Suitable amphoteric detersive surfactants include those surfactants broadly described as derivatives of aliphatic secondary and tertiary amines in which the aliphatic radical can be straight or branched chain and wherein one of the aliphatic substituents contains from 8 to 18 carbon atoms and one contains an anionic group such as carboxy, sulfonate, sulfate, phosphate, or phosphonate. Suitable amphoteric detersive surfactants for use in the present invention include, but are not limited to: cocoamphoacetate, cocoamphodiacetate, lauroamphoacetate, lauroamphodiacetate, and mixtures thereof.

Preferably surfactants comprising saturated alkyl chains are used.

The Enzyme System

The laundry detergent composition of the present invention comprises an enzyme cocktail, wherein the enzyme cocktail comprises a xanthan endoglucanase, a xanthan lyase, and a mannanase.

Enzyme Definitions

Parent: The term "parent" means an enzyme from which an alteration is made to produce the enzyme variants. The parent may be a naturally occurring (wild-type) polypeptide or a variant thereof.

Sequence Identity: The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

Alternatively, the parameters used may be gap open penalty of 10, gap extension penalty of 0.5, and the EDNAFULL (EMBOSS version of NCBI NUC4.4) substitution matrix. The output of Needle labelled "longest identity" (obtained using the -nobrief option) is used as the percent identity and is calculated as follows:

(Identical Deoxyribonucleotides×100)/(Length of Alignment−Total Number of Gaps in Alignment)

Variant: The term "variant" means a polypeptide having enzyme activity comprising an alteration/mutation, i.e., a substitution, insertion, and/or deletion, at one or more (e.g. several) positions relative to the parent enzyme. A substitution means a replacement of an amino acid occupying a position with a different amino acid; a deletion means removal of an amino acid occupying a position; and an insertion means adding 1-3 amino acids adjacent to and immediately following an amino acid occupying a position. Alterations/mutations are typically described using single letter amino acid codes and notation that is familiar to those skilled in the art. For example, S23D defines a substation of a serine (S) residue at position 23 with aspartic acid (D); Y30* defines a deletion of the tyrosine residue at position 30. G34GW defines an insertion of a tryptophan residue after the glycine at position 34.

Wild-Type Enzyme: The term "wild-type" means an enzyme encoded by the DNA of a naturally occurring organism, such as a bacterium, yeast, or filamentous fungus found in nature.

The Xanthan Endoglucanase

As used herein, the term xanthan endoglucanase denotes an enzyme exhibiting endo-beta-1,4-glucanase activity that is capable of catalysing hydrolysis of the 1,4-linked β-D-glucose polymeric backbone of xanthan gum in conjunction with a suitable xanthan lyase enzyme. The xanthan endoglucanase in accordance with the invention has endo-beta-1,4-glucanase activity and a polypeptide having at least 60% identity to SEQ ID NO: 1. SEQ ID NO: 1 corresponds to the amino acid sequence of a xanthan endoglucanase endogenous to *Paenibacillus* sp-62047 In further embodiments of the invention, the xanthan endoglucanase is variant with at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 1.

In further embodiments of the invention, the xanthan endoglucanase has substitutions at one or more of positions 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 605, 609, 676, 688, 690, 694, 697, 698, 699, 711, 719, 754, 756, 760, 781, 786, 797, 833, 834, 835 and 1048 of SEQ ID NO: 1.

In further embodiments of the invention, the xanthan endoglucanase has substitutions at one or more of positions S17A, F20P, F20N, F20G, F20Y, K51Q, K51H, E53P, E53G, Y55M, V56M, Y60F, S63F, T87R, A186P, K192N, I320D, I302H, I302V, I302M, H311N, S313D, I387T, K388R, K390Q, I403Y, E408D, E408S, E408P, E408A, E408G, E408N, P410G, Q416S, Q416D, A448E, A448W, A448S, K451S, G471S, S472Y, D476R, Q489P, K507R, K512P, S515V, S538C, Y579W, S598Q, A599S, I602T, I602D, V603P, S605T, G609E, D676H, A688G, Y690F, T694A, T697G, R698W, T699A, T711V, T711Y, W719R, K754R, V756H, V756Y, S760G, T781M, N786K, T797S, A824D, N833D, Q834E, S835D and F1048W Examples of suitable xanthan endoglucanases in accordance with the invention are listed below, wherein the substitutions correspond to positions in SEQ ID NO: 1:

| Variant # | Mutations |
|---|---|
| 1 | S17A, F20P, N216D, A283D, H311N, E408D, Y579W, I602T, A651P, A688G, T883R, F906A, Y934G, Q956Y |
| 2 | F20P, I302D, S313D, E408D, D476R, Y579W, S636K, T697G, V756Y, V881Q, T887F, F906A, A937E |
| 3 | F20P, S313D, E408D, Y579W, S636K, A688G, T697G, N905D, A937E |
| 4 | F20P, I302D, S313D, E408D, D476R, Y579W, S636K, T697G, W719R, V756Y, V881Q, T887K, F906A, A937E |
| 5 | N216Q, S313D, E408D, D476R, Y579W, I602T, F638N, A651P, T697G, W719R, R880K, T887K, K921R, Y934G |
| 6 | N216D, S313D, E408D, D476R, A564E, Y579W, I602T, F638N, A651P, Y690F, T697G, W719R, V756H, N833D, A869V, R880K, V881T, T887K, K921R, S928D, Y934G, T999R |
| 7 | F20P, I302D, S313D, E408D, D476R, Y579W, S636K, T697G, W719R, V756Y, N848D, A869V, V881Q, T887K, N905D, F906A, Q912V, A937E, T999R, F1048W |
| 8 | F20P, I302D, S313D, E408D, D476R, Q489P, Y579W, S636K, T697G, W719R, V756Y, A824D, N848D, V881Q, T887K, F906A, S928D, A937E |
| 9 | F20P, I302D, S313D, E408D, Q416S, D476R, Q489P, Y579W, I602T, S636K, A651P, T697G, W719R, V756Y, A824D, N833D, N848D, T883R, T887K, F906A, A937E |
| 10 | F20P, A186P, I302D, S313D, E408D, D476R, Q489P, Y579W, A599S, I602T, S636K, A651P, T697G, W719R, V756Y, N848D, T883R, T887K, F906A, A937E |
| 11 | N216D, S313D, E408D, D476R, Y579W, I602T, V603P, F638N, A651P, A688G, T697G, W719R, V756H, R880K, T887K, K921 R, S928D, Y934G, K948R |
| 12 | F20P, K51Q, I302D, S313D, E408D, D476R, Q489P, Y579W, I602T, S636K, A651P, T697G, W719R, V756Y, N848D, T883R, T887K, F906A, A937E |
| 13 | F20P, I302D, S313D, A346D, E408D, D476R, Q489P, Y579W, S636N, T697G, W719R, V756Y, A824D, N848D, V881Q, T887K, F906A, A937E, T999R |
| 14 | F20P, I302D, S313D, E408D, D476R, Q489P, Y579W, I602T, S636N, T697G, W719R, V756Y, A824D, N848D, V881Q, T887K, N905D, F906A, A937E, T999R, A1037E, F1048W |
| 15 | F20P, K51Q, I302D, S313D, E408D, D476R, Q489P, Y579W, I602T, S636K, A651P, T697G, W719R, V756Y, A824D, N848D, T883R, T887K, F906A, S928D, A937E, A1037E |
| 16 | N216D, S313D, A346D, E408D, D476R, Q489P, A559P, Y579W, I602T, F638N, A651P, A688G, T697G, W719R, V756H, R880K, T887K, K921R, S928D, Y934G |
| 17 | F20P, I302D, S313D, A346D, E408D, D476R, Q489P, Y579W, I602T, T697G, W719R, V756Y, N848D, V881Q, T887K, F906A, A937E |
| 18 | N216D, S313D, E408D, D476R, Q489P, A559P, Y579W, I602T, F638N, A651P, A688G, T697G, W719R, V756H, Q834E, R880K, T887K, T892P, K921R, S928D, Y934G |
| 19 | F20P, I302D, S313D, E408D, D476R, Q489P, A559N, Y579W, I602T, S636K, A651P, T697G, W719R, V756Y, N848D, T883R, T887K, F906A, S928D, A937E |
| 20 | F20P, I302D, S313D, E408D, D476R, Q489P, Y579W, I602T, S636K, A651P, T697G, W719R, V756Y, N848D, T883R, T887K, F906A, A937E |
| 21 | F20P, I302D, S313D, E408D, Q416S, D476R, Q489P, A559N, Y579W, I602T, S636K, A651P, T697G, W719R, V756Y, N848D, T883R, T887K, F906A, A937E |
| 22 | F20P, I302D, S313D, E408D, D476R, Y579W, I602T, S636N, T697G, W719R, V756Y, A824D, N848D, V881Q, T887K, F906A, S928D, A937E, T999R, F1048W |

The Xanthan Lyase

As used herein, the term "xanthan lyase" denotes an enzyme that cleaves the β-D-mannosyl-β-D-1,4-glucuronosyl bond of xanthan and have been described in the literature. Xanthan lyases are classified according to the Enzyme Nomenclature as EC 4.2.2.12, and are known to be produced by many xanthan-degrading bacteria including *Bacillus*, *Corynebacterium* and *Paenibacillus* species. The xanthan lyase in accordance with the invention has xanthan lyase activity and comprises a polypeptide having at least 60% identity to SEQ ID NO: 2. SEQ ID NO: 2 corresponds to the amino acid sequence of a xanthan lyase endogenous to a *Paenibacillus* sp.

In further embodiments of the invention, the xanthan lyase is a variant with at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2.

In another embodiment of the invention, the xanthan lyase is a variant with alterations at one or more positions selected from the group consisting of positions: 9, 15, 46, 58, 66, 89, 95, 100, 106, 109, 183, 188, 190, 203, 204, 221, 229, 234, 238, 240, 242, 243, 257, 258, 291, 293, 316, 320, 324, 329, 333, 339, 341, 352, 354, 360, 377, 399, 400, 419, 440, 450, 451, 454, 458, 481, 492, 567, 568, 578, 579, 582, 664, 672, 703, 728, 843, 855, 887, 892, 1008 and 1016 of SEQ ID NO: 2. In another embodiment of the invention, the xanthan lyase is a variant with alterations at one or more positions selected from the group consisting of positions 624, 631, 635, 649, 656, 752, 752, 754, 757, 769, 775, 777, 800, 801, 875, 911, and 915 of SEQ ID NO: 2.

In another embodiment of the invention, the xanthan lyase is a variant with one or more substitutions selected from the group consisting of: K9R, N15T, L46D, A58L, S66H, Q89Y, K95E, S100D, N106Y, Q109R, Q109D, Q109F, Q109K, Q109A, K183Q, K183R, V188I, A190Q, A203P, K204R, A221P, E229N, E229S, I234V, I238W, I238L, I238M, I240W, N242S, G243V, Y257W, R258E, K291R, A293G, A293P, K316R, K320R, L324Q, K329R, K333R, L339M, I341P, V352I, S354P, K360G, K360R, F377Y, N399K, K400R, F419Y, N440K, D450P, K451E, K451R, A454V, D458S, K481R, A492L, A492H, K567R, G568A, S578K, S578R, S579R, S579K, S582K, A624E, T631N, S635E, T649K, I656V, T664K, N672D, I703L, M728V, G738L, P752K, P752R, G753E, S754E, S754R, S757D, A769D, L775A, D777R, V800P, D801 G, A843P, K855R, K875T, K887R, N892Y, N892W, N892F, A911V, T915A, N1008D and K1016T of SEQ ID NO: 2.

In another embodiment of the invention, the xanthan lyase is a variant with one of the following sets of substitutions, based on SEQ ID NO: 2.

| Variant # | Mutations |
|---|---|
| 1 | A190Q, E229S, S635E, T649K, I656V, N672D, I703L, G753E, S754E, S757D, A769D, L775A, D801G, K875T, N892Y, N1008D |
| 2 | E229S, S635E, T649K, I656V, N672D, I703L, G753E, S754E, A769D, L775A, D801G, K875T, N892Y, N1008D |

-continued

| Variant # | Mutations |
|---|---|
| 3 | E229S, V352I, S635E, T649K, I656V, N672D, G753E, S754E, A769D, L775A, V800P, D801G, K875T, N892Y |
| 4 | E229S, K360G, D458S, S582K, N672D, G753E, S754E, A769D, L775A, D801G, K875T, N892Y, N1008D |
| 5 | S100D, E229S, K360G, D458S, S582K, T664K, N672D, G753E, S754E, S757D, A769D, L775A, D801G, A843P, K875T, N892Y, A911V, N1008D, K1016T |
| 6 | E229S, I234V, S582K, N672D, G753E, S754E, A769D, L775A, V800P, D801G, K875T, N892Y |
| 7 | Q89Y, E229S, N440K, S582K, A624E, N672D, G753E, S754E, A769D, L775A, D801G, K875T, N892Y |
| 8 | E229S, S635E, T649K, I656V, N672D, P752K, G753E, A769D, L775A, D801G, A843P, K875T, N892Y |
| 9 | E229S, S635E, T649K, I656V, N672D, G753E, S754E, S757D, A769D, L775A, D801G, K875T, N892Y |
| 10 | E229S, N440K, S582K, N672D, G753E, S754E, A769D, L775A, D801G, A843P, K875T, N892Y, N1008D |
| 11 | E229S, N440K, S582K, A624E, N672D, G753E, S754E, A769D, L775A, V800P, D801G, K875T, N892Y |
| 12 | A190Q, E229S, S635E, T649K, I656V, N672D, P752K, G753E, A769D, L775A, D801G, A843P, K875T, N892Y |
| 13 | A190Q, E229S, S582K, N672D, G753E, S754E, A769D, L775A, D801G, K875T, N892Y |
| 14 | E229S, N440K, S582K, N672D, P752R, G753E, S754E, S757D, A769D, L775A, D801G, K875T, N892Y, N1008D |
| 15 | E229S, S582K, S635E, N672D, P752R, G753E, S754E, A769D, L775A, D801G, K875T, N892Y, N1008D |
| 16 | A190Q, E229S, N440K, S582K, A624E, S635E, N672D, G753E, S754E, A769D, L775A, D801G, K875T, N892Y |
| 17 | E229S, I234V, A492L, S582K, N672D, G753E, S754E, A769D, L775A, D801G, K875T, N892Y |
| 18 | A190Q, E229S, K360G, D458S, S582K, T664K, N672D, G753E, S754E, A769D, L775A, D801G, K875T, N892Y, N1008D |
| 19 | S100D, E229S, K360G, D458S, S582K, N672D, G753E, S754E, S757D, A769D, L775A, D801G, A843P, K875T, N892Y, T915A, N1008D |
| 20 | E229S, N440K, S582K, A624E, S635E, N672D, G738L, G753E, S754E, S757D, A769D, L775A, D801G, K875T, N892Y |
| 21 | S100D, E229S, K360G, D458S, S582K, N672D, G753E, S754E, A769D, L775A, D801G, K875T, N892Y, N1008D |
| 22 | A190Q, E229S, D458S, T631N, N672D, G753E, S754E, A769D, L775A, D801G, A843P, K875T, N892Y |
| 23 | A190Q, E229S, K360G, D458S, S582K, N672D, G753E, S754E, A769D, L775A, D801G, K875T, N892Y, N1008D |
| 24 | E229S, S635E, T649K, I656V, N672D, G753E, S754R, S757D, A769D, L775A, D801G, A843P, K875T, N892Y |
| 25 | E229S, D458S, S582K, T631N, S635E, N672D, M728V, G753E, S754E, S757D, A769D, L775A, D801G, K875T, N892Y |
| 26 | A190Q, E229S, K360G, D458S, S582K, N672D, G753E, S754E, S757D, A769D, L775A, D801G, K875T, N892Y, N1008D |
| 27 | E229S, A492L, S635E, T649K, I656V, N672D, G753E, S757D, A769D, L775A, D801G, K875T, N892Y |
| 28 | S100D, A190Q, E229S, K360G, D458S, S582K, N672D, G753E, S754E, A769D, L775A, D801G, K875T, N892Y, N1008D |
| 29 | A190Q, E229S, I234V, S582K, N672D, G753E, S754E, S757D, A769D, L775A, D801G, K875T, N892Y |
| 30 | E229S, N399K, D458S, A492H, K567R, S582K, S635E, T649K, N672D, G753E, S754E, A769D, L775A, D777R, D801G, K875T, N892Y |
| 31 | E229S, D458S, A492L, T631N, N672D, G753E, S754E, S757D, A769D, L775A, D801G, K875T, N892Y |
| 32 | E229S, D458S, A492H, K567R, S582K, S635E, N672D, G753E, S754E, A769D, L775A, D777R, D801G, K875T, N892Y |
| 33 | S100D, E229S, K360G, D458S, S582K, N672D, G753E, S754E, S757D, A769D, L775A, D801G, A843P, K875T, N892Y, N1008D |
| 34 | E229S, N399K, D458S, K567R, S582K, S635E, N672D, G753E, S754E, A769D, L775A, D777R, D801G, K875T, N892Y |

The Mannanase

As used herein, the term "mannanase" or "galactomannanase" denotes a mannanase enzyme defined according to that known in the art as mannan endo-1,4-beta-mannosidase and having the alternative names beta-mannanase and endo-1,4-mannanase and catalysing hydrolysis of 1,4-beta-D-mannosidic linkages in mannans, galactomannans, glucomannans, and galactoglucomannans. Mannanases are classified according to the Enzyme Nomenclature as EC 3.2.1.78.

Suitable mannanase can be selected from the group consisting of:
  a) mannanase having mannanase activity and a polypeptide having at least 85% sequence identity to residues 27-331 of SEQ ID NO: 3. SEQ ID NO: 3 corresponds to the full-length amino acid sequence of the Man7 mannanase endogenous to *Bacillus hemicellulosilyticus* including a signal sequence;
  b) mannanase has mannanase activity and a polypeptide having at least 60% identity to SEQ ID NO: 4. In one embodiment of the invention, the mannanase has mannanase activity and a polypeptide having at least 80% identity to SEQ ID NO: 4. SEQ ID NO: 4 corresponds to the full-length amino acid sequence of the Man4 mannanase endogenous to *Paenibacillus* sp;
  c) and mixtures thereof.

As such, suitable mannanase can have mannanase activity and a polypeptide having at least 85% sequence identity to residues 27-331 of SEQ ID NO: 3. SEQ ID NO: 3 corresponds to the full-length amino acid sequence of the Man7 mannanase endogenous to *Bacillus hemicellulosilyticus* including a signal sequence. In one embodiment of the invention, the mannanase has at least 90% sequence identity to residues 27-331 of SEQ ID NO: 3. In another embodiment of the invention, the mannanase is a variant of SEQ ID NO: 3 comprising at least one substitution at positions 123, 158, 180, 272, 285, or 307 or a combination thereof. In another embodiment of the invention, the mannanase is a variant of SEQ ID NO: 3 comprising at least one substitution at positions M123, A158, F180, G272, T285, or T307 or a combination thereof. In another embodiment of the invention, the mannanase is a variant of SEQ ID NO: 3 comprising at least one substitution at positions M123, A158, F180, G272, T307, or L316, or a combination thereof. In an embodiment the variant comprises one further substitution, two further substitutions, three further substitutions or four further substitutions.

Alternatively, or in addition, suitable mannanase can have mannanase activity and a polypeptide having at least 60% identity to SEQ ID NO: 4. In one embodiment of the invention, the mannanase has mannanase activity and a polypeptide having at least 80% identity to SEQ ID NO: 4. SEQ ID NO: 4 corresponds to the full-length amino acid sequence of the Man4 mannanase endogenous to *Paenibacillus* sp.

The mannanase can be a variant of SEQ ID NO: 4 comprising one, two, three, four, five, six, seven or more variations versus SEQ ID NO: 4 selected from:
  (i) N10Q/T, P19E/V, S30T, T38E/I/L/M/Q/R/V, S59D/G/K/N/Q/T, L60F/M/V, T62E/I/Q/V, K63L, L66C/T/V, N67A/D/E/G/P/Q/S/V, A68L/M/R/S/W, K70R/V, N71D/H, N74E/C/Q/V, V75I, Q78A/D/L/M, N79E/F/W, K80Q/T, N97E/L/P/Q, V103I, Y129M, T131P, S135A/C/Q, A136E, K143Q/R, F167L/S/W/Y, P168A/E/G/L/M/S/T, Q184D/F/H/L/M/P, N213E, K214C/Q, G225A/C/P/W, T228A/G/H/I/K/S/V/Y, Y235G/I/L/Q/

S/V, Q242S/E, K244A/C/G/L/M/P/S, S258A/D/E/G/M/N/P/T, G259A/E/R/S/W, N261I/M/P/Q/R/S/T/V/W/Y, and D283G/H/T; or (ii) P19E/V, T38E/I/L/M/Q/R/V, N67A/D/E/G/P/Q/S/V, N97E/L/P/Q, Y129M, K143Q/R, P168A/E/G/L/M/S/T, Q184D/F/H/L/M/P, G225A/C/P/W, T228A/G/H/I/K/S/V/Y, Y235G/I/L/Q/S/V, K244A/C/G/L/M/P/S, S258A/D/E/G/M/N/P/T, and N261I/M/P/Q/R/S/T/V/W/Y; or (iii) P19E/V, T38E/I/L/M/Q/R/V, N67A/D/E/G/P/Q/S/V, L85L, Y129M, P168A/E/G/L/M/S/T, Q184D/F/H/L/M/P, G225A/C/P/W, K244A/C/G/L/M/P/S, S258A/D/E/G/M/N/P/T, and N261I/M/P/Q/R/S/T/V/W/Y; or (iv) P19E, S30T, T38E, S59V, L60Q, K63R, N67D, N97D, V103I, Y129M, F167Y, P168S, Q184L, G225C, T228V, Y235L, K244L, S258D, and N261R;

with the proviso that one or more of said variations is non-naturally occurring; and wherein the amino acid positions of said mannanase variant or recombinant polypeptide or active fragment thereof are numbered by correspondence with the amino acid sequence of SEQ ID NO:4.

Alternatively, or in addition, the mannanase can be a variant of SEQ ID NO: 4 comprising a combination of variations to SEQ ID NO:4 selected from P19E-T38E-N67D-N97D-Y129M-P168S-Q184L-K244L-S258D-N261R; N10T-P19E-G28S-S30T-T38E-N67D-N71D-N97D-Y129M-P168S-Q184L-G225C-Y235L-K244L-S258D-N261R-F297FQ; P19E-S30T-T38E-S59V-L60Q-K63R-N67D-N97D-V103I-Y129M-F167Y-Q184L-G225C-T228V-Y235L-K244L-S258D-N261R-F297FQ; N10T-P19E-S30T-T38E-S59V-L60Q-K63R-N67D-N97D-Y129M-K143Q-P168S-Q184L-G225C-T228V-Y235L-K244L-S258D-N261R-F297FQ; N10T-P19E-S30T-T38E-S59V-L60Q-K63R-N67D-N97D-Y129M-K143Q-P168S-Q184L-G225P-T228V-Y235L-K244L-S258D-N261R-F297FQ; N10T-P19E-S30T-T38E-S59V-L60Q-K63R-N67D-N71D-N97D-V103I-Y129M-K143Q-P168S-Q184L-G225P-T228V-Y235L-K244L-S258D-N261R-F297FQ; A2S-P19E-G28S-S30T-T38E-K63R-N67D-N71D-N74E-K93R-N97D-Y129M-N150T-P168S-Q184L-N213A-G225C-Y235L-K244L-S258D-N261Q-F297FQ; T3R-N10T-P19E-G28A-S30T-T38E-T62E-N67D-N71D-K93R-N97L-E111S-Y129M-D139M-P168S-Q184L-G225C-Y235L-K244L-S258D-N261Q-F297FQ; and N10T-P19E-G28A-S30T-T38E-S59D-N67D-A68S-N71D-K93R-N97D-Y129M-K143Q-P168S-Q184D-G225C-Y235L-K244L-S258D-N261R-T284E-F297FQ; and wherein the amino acid positions of said mannanase variant are numbered by correspondence with the amino acid sequence of SEQ ID NO:4. Mannanase activity can be confirmed using readily available assay kits, including those commercially available from Megazyme, Bray, Ireland and Glycospot, Søborg, Denmark.

Lipase

The enzyme system preferably further comprises a lipase. The presence of oils and/or grease can further increase the resiliency of stains comprising mannans and other polysaccharides. As such, the presence of lipase in the enzyme package can further improve the removal of such stains. Suitable lipases include those of bacterial, fungal or synthetic origin, and variants thereof. Chemically modified or protein engineered mutants are also suitable. Examples of suitable lipases include lipases from H1-umicola (synonym Thermomyces), e.g., from *H. lanuginosa* (*T. lanuginosus*).

The lipase may be a "first cycle lipase", e.g. such as those described in WO06/090335 and WO 13/116261. In one aspect, the lipase is a first-wash lipase, preferably a variant of the wild-type lipase from *Thermomyces lanuginosus* comprising T231R and/or N233R mutations.

Preferred lipases include those sold under the tradenames Lipex®, Lipolex® and Lipoclean® by Novozymes, Bagsvaerd, Denmark.

Other suitable lipases include: Liprl 139, e.g. as described in WO2013/171241; TfuLip2, e.g. as described in WO2011/084412 and WO2013/033318; *Pseudomonas stutzeri* lipase, e.g. as described in WO2018228880; *Microbulbifer thermotolerans* lipase, e.g. as described in WO2018228881; *Sulfobacillus acidocaldarius* lipase, e.g. as described in EP3299457; LIP062 lipase e.g. as described in WO2018209026; PinLip lipase e.g. as described in WO2017036901 and *Absidia* sp. lipase e.g. as described in WO2017005798.

A suitable lipase is a variant of SEQ ID NO:5 comprising:
(a) substitution T231R
and
(b) substitution N233R or N233C
and
(c) at least three further substitutions selected from E1C, D27R, N33Q, G38A, F51V, G91Q, D96E, K98L, K98I, D111A, G163K, H198S, E210Q, Y220F, D254S, I255A, and P256T;
where the positions correspond to the positions of SEQ ID NO:5 and wherein the lipase variant has at least 90% but less than 100% sequence identity to the polypeptide having the amino acid sequence of SEQ ID NO: 5 and wherein the variant has lipase activity.

One preferred lipase is a variant of SEQ ID NO: 5 comprising the following substitutions: T231R, N233R, D27R, G38A, D96E, D111A, G163K, D254S and P256T One preferred lipase is a variant of SEQ ID NO: 5 comprising the following substitutions: T231R, N233R, N33Q, G91Q, E210Q, I255A.

Suitable lipases are commercially available from Novozymes, for example as Lipex Evity 100 L, Lipex Evity 200 L (both liquid raw materials) and Lipex Evity 105T (a granulate). These lipases have different structures to the products Lipex 100 L, Lipex 100T and Lipex Evity 100T which are outside the scope of the invention.

Other Enzymes

The enzyme system can comprise other enzymes. Suitable enzymes provide cleaning performance and/or fabric care benefits. Examples of other suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and known amylases, or combinations thereof. A preferred enzyme system further comprises a cocktail of conventional detersive enzymes such as protease, lipase, cutinase and/or cellulase in conjunction with amylase. Detersive enzymes are described in greater detail in U.S. Pat. No. 6,579,839.

Optional Ingredients

The detergent composition may additionally comprise one or more of the following optional ingredients: external structurant or thickener, enzymes, enzyme stabilizers, cleaning polymers, bleaching systems, optical brighteners, hueing dyes, particulate material, perfume and other odour control agents, hydrotropes, suds suppressors, fabric care benefit agents, pH adjusting agents, dye transfer inhibiting agents, preservatives, non-fabric substantive dyes and mixtures thereof. In more preferred embodiments, the laundry detergent composition does not comprise a bleach.

External structurant or thickener: Preferred external structurants and thickeners are those that do not rely on charge-charge interactions for providing a structuring benefit. As such, particularly preferred external structurants are uncharged external structurants, such as those selected from the group consisting of: non-polymeric crystalline, hydroxyl functional structurants, such as hydrogenated castor oil; microfibrillated cellulose; uncharged hydroxyethyl cellulose; uncharged hydrophobically modified hydroxyethyl cellulose; hydrophobically modified ethoxylated urethanes; hydrophobically modified non-ionic polyols; and mixtures thereof.

Suitable polymeric structurants include naturally derived and/or synthetic polymeric structurants. Examples of naturally derived polymeric structurants of use in the present invention include: microfibrillated cellulose, hydroxyethyl cellulose, hydrophobically modified hydroxyethyl cellulose, carboxymethyl cellulose, polysaccharide derivatives and mixtures thereof. Non-limiting examples of microfibrillated cellulose are described in WO 2009/101545 A1. Suitable polysaccharide derivatives include: pectine, alginate, arabinogalactan (gum Arabic), carrageenan, gellan gum, xanthan gum, guar gum and mixtures thereof.

Examples of synthetic polymeric structurants or thickeners of use in the present invention include: polycarboxylates, hydrophobically modified ethoxylated urethanes (HEUr), hydrophobically modified non-ionic polyols and mixtures thereof.

Preferably, the aqueous liquid detergent composition has a viscosity of 50 to 5,000, preferably 75 to 1,000, more preferably 100 to 500 mPa·s, when measured at a shear rate of 100 s−1, at a temperature of 20° C. For improved phase stability, and also improved stability of suspended ingredients, the aqueous liquid detergent composition has a viscosity of 50 to 250,000, preferably 5,000 to 125,000, more preferably 10,000 to 35,000 mPa·s, when measured at a shear rate of 0.05 s−1, at a temperature of 20° C.

Cleaning polymers: The detergent composition preferably comprises a cleaning polymer. Such cleaning polymers are believed to at least partially lift the stain from the textile fibres and enable the enzyme system to more effectively break up the complexes comprising mannan and other polysaccharide. Suitable cleaning polymers provide for broad-range soil cleaning of surfaces and fabrics and/or suspension of the soils. Non-limiting examples of suitable cleaning polymers include: amphiphilic alkoxylated grease cleaning polymers; clay soil cleaning polymers; soil release polymers; and soil suspending polymers. A preferred cleaning polymer is obtainable by free-radical copolymerization of at least one compound of formula (I),

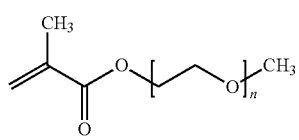
(I)

in which n is equal to or greater than 3 for a number, with at least one compound of formula (II),

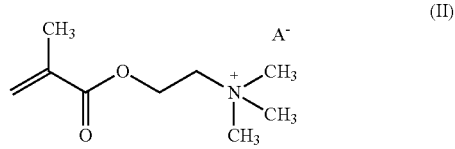
(II)

in which A⁻ represents an anion, in particular selected from halides such as fluoride, chloride, bromide, iodide, sulfate, hydrogen sulfate, alkyl sulfate such as methyl sulfate, and mixtures thereof. Such polymers are further described in EP3196283A1.

For similar reasons, polyester based soil release polymers, such as SRA300, supplied by Clariant are also particularly preferred.

Other useful cleaning polymers are described in USPN 2009/0124528A1. The detergent composition may comprise amphiphilic alkoxylated grease cleaning polymers, which may have balanced hydrophilic and hydrophobic properties such that they remove grease particles from fabrics and surfaces. The amphiphilic alkoxylated grease cleaning polymers may comprise a core structure and a plurality of alkoxylate groups attached to that core structure. These may comprise alkoxylated polyalkyleneimines, for example. Such compounds may comprise, but are not limited to, ethoxylated polyethyleneimine, ethoxylated hexamethylene diamine, and sulfated versions thereof. Polypropoxylated derivatives may also be included. A wide variety of amines and polyalklyeneimines can be alkoxylated to various degrees. A useful example is 600 g/mol polyethyleneimine core ethoxylated to 20 EO groups per NH and is available from BASF. The alkoxylated polyalkyleneimines may have an inner polyethylene oxide block and an outer polypropylene oxide block. The detergent compositions may comprise from 0.1% to 10%, preferably, from 0.1% to 8%, more preferably from 0.1% to 2%, by weight of the detergent composition, of the cleaning polymer.

Dye transfer inhibitor: The detergent composition can comprise a dye transfer inhibitor. Suitable dye transfer inhibitors can be selected from the group consisting of polyvinylpyrrolidone (PVP), polyvinylimidazole (PVI), copolymers of vinylpyrrolidone and vinylimidazole (PVP/PVI), polyvinyl pyridine-N-oxide, poly-N-carboxymethyl-4-vinylpyridiumchloride, and mixtures thereof, with polyvinylpyrrolidone (PVP), polyvinylimidazole (PVI), copolymers of vinylpyrrolidone and vinylimidazole (PVP/PVI), and mixtures thereof being particularly preferred. The dye transfer inhibitor can be present at a level of from 0.05% to 5%, preferably from 0.1% to 3%, and more preferably from 0.2% to 2.5%, by weight of the detergent composition.

Polymer Deposition Aid: The laundry detergent composition can comprise from 0.1% to 7%, more preferably from 0.2% to 3%, of a polymer deposition aid. As used herein, "polymer deposition aid" refers to any cationic polymer or combination of cationic polymers that significantly enhance deposition of a fabric care benefit agent onto the fabric during laundering. Suitable polymer deposition aids can comprise a cationic polysaccharide and/or a copolymer, with cationic polysaccharide being preferred and polyquaternium 7 being most preferred. "Fabric care benefit agent" as used herein refers to any material that can provide fabric care benefits. Non-limiting examples of fabric care benefit agents include: silicone derivatives, oily sugar derivatives, dispersible polyolefins, polymer latexes, cationic surfactants and combinations thereof. Preferably, the deposition aid is a cationic or amphoteric polymer. The cationic charge density of the polymer preferably ranges from 0.05 milliequivalents/g to 6 milliequivalents/g. The charge density is calculated by dividing the number of net charge per repeating unit by the molecular weight of the repeating unit. In one embodiment, the charge density varies from 0.1 milliequivalents/g to 3 milliequivalents/g. The positive charges could be on the backbone of the polymers or the side chains of polymers.

Organic builder and/or chelant: The laundry detergent composition can comprise from 0.6% to 10%, preferably from 2 to 7% by weight of one or more organic builder and/or chelants. Suitable organic builders and/or chelants are selected from the group consisting of: MEA citrate, citric acid, aminoalkylenepoly(alkylene phosphonates), alkali metal ethane 1-hydroxy disphosphonates, and nitrilotrimethylene, phosphonates, diethylene triamine penta (methylene phosphonic acid) (DTPMP), ethylene diamine tetra (methylene phosphonic acid) (DDTMP), hexamethylene diamine tetra(methylene phosphonic acid), hydroxy-ethylene 1,1 diphosphonic acid (HEDP), hydroxyethane dimethylene phosphonic acid, ethylene di-amine di-succinic acid (EDDS), ethylene diamine tetraacetic acid (EDTA), hydroxyethylethylenediamine triacetate (HEDTA), nitrilotriacetate (NTA), methylglycinediacetate (MGDA), iminodisuccinate (IDS), hydroxyethyliminodisuccinate (HIDS), hydroxyethyliminodiacetate (HEIDA), glycine diacetate (GLDA), diethylene triamine pentaacetic acid (DTPA), catechol sulfonates such as Tiron™ and mixtures thereof.

Enzyme stabiliser: Enzymes can be stabilized using any known stabilizer system such as calcium and/or magnesium compounds, boron compounds and substituted boric acids, aromatic borate esters, peptides and peptide derivatives, polyols, low molecular weight carboxylates, relatively hydrophobic organic compounds [e.g. certain esters, diakyl glycol ethers, alcohols or alcohol alkoxylates], alkyl ether carboxylate in addition to a calcium ion source, benzamidine hypochlorite, lower aliphatic alcohols and carboxylic acids, N,N-bis(carboxymethyl) serine salts; (meth)acrylic acid-(meth)acrylic acid ester copolymer and PEG; lignin compound, polyamide oligomer, glycolic acid or its salts; poly hexa methylene bi guanide or N,N-bis-3-amino-propyl-dodecyl amine or salt; and mixtures thereof.

Hueing dyes: The detergent composition may comprise fabric hueing agent (sometimes referred to as shading, bluing, or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and combinations thereof.

Optical brighteners: The detergent composition may comprise, based on the total detergent composition weight, from 0.005 to 2%, preferably 0.01 to 0.1% of a fluorescent agent (optical brightener). Fluorescent agents are well known and many fluorescent agents are available commercially. Usually, these fluorescent agents are supplied and used in the form of their alkali metal salts, for example, the sodium salts. Preferred classes of fluorescent agent are: Di-styryl biphenyl compounds, e.g. Tinopal (Trade Mark) CBS-X, Di-amine stilbene di-sulphonic acid compounds, e.g. Tinopal DMS pure Xtra and Blankophor (Trade Mark) HRH, and Pyrazoline compounds, e.g. Blankophor S N. Preferred fluorescers are: sodium 2-(4-styryl-3-sulfophenyl)-2H-napthol[1,2-d]trazole, disodium 4,4'-bis{[(4-anilino-6-(N methyl-N-2 hydroxyethyl)amino 1,3,5-triazin-2-yl)]amino}stilbene-2-2' disulfonate, disodium 4,4'-bis{[(4-anilino-6-morpholino-1,3,5-triazin-2-yl)]amino}stilbene-2-2' disulfonate, and disodium 4,4'-bis(2-sulfoslyryl)biphenyl.

Hydrotrope: The detergent composition may comprise, based on the total detergent composition weight, from 0 to 30%, preferably from 0.5 to 5%, more preferably from 1.0 to 3.0%, which can prevent liquid crystal formation. The addition of the hydrotrope thus aids the clarity/transparency of the composition. Suitable hydrotropes comprise but are not limited to urea, salts of benzene sulphonate, toluene sulphonate, xylene sulphonate or cumene sulphonate. Preferably, the hydrotrope is selected from the group consisting of propylene glycol, xylene sulfonate, ethanol, and urea to provide optimum performance.

Particles: The composition can also comprise particles, especially when the composition further comprises a structurant or thickener. The composition may comprise, based on the total composition weight, from 0.02% to 10%, preferably from 0.1% to 4%, more preferably from 0.25% to 2.5% of particles. Said particles include beads, pearlescent agents, microcapsules, and mixtures thereof.

Microcapsules: Suitable capsules are typically formed by at least partially, preferably fully, surrounding a benefit agent with a wall material. Preferably, the capsule is a perfume capsule, wherein said benefit agent comprises one or more perfume raw materials. The capsule wall material may comprise: melamine, polyacrylamide, silicones, silica, polystyrene, polyurea, polyurethanes, polyacrylate based materials, polyacrylate esters based materials, gelatin, styrene malic anhydride, polyamides, aromatic alcohols, polyvinyl alcohol, resorcinol-based materials, poly-isocyanate-based materials, acetals (such as 1,3,5-triol-benzene-gluteraldehyde and 1,3,5-triol-benzene melamine), starch, cellulose acetate phthalate and mixtures thereof. Preferably, the capsule wall comprises melamine and/or a polyacrylate based material. The perfume capsule may be coated with a deposition aid, a cationic polymer, a non-ionic polymer, an anionic polymer, or mixtures thereof. Preferably, the perfume capsules have a volume weighted mean particle size from 0.1 microns to 100 microns, preferably from 0.5 microns to 60 microns. Especially where the composition comprises capsules having a shell formed at least partially from formaldehyde, the composition can additionally comprise one or more formaldehyde scavengers.

Process of Making the Laundry Detergent Composition:

The laundry detergent compositions can be made using any suitable process known to the skilled person. Typically, the ingredients are blended together in any suitable order. Preferably, the detersive surfactants are added as part of a concentrated premix, to which are added the other optional ingredients. Preferably, the solvent is added either last, or if an external structurant is added, immediately before the external structurant, with the external structurant being added as the last ingredient.

Method of Laundering Fabrics:

The laundry detergent compositions of the present invention can be used to launder fabrics. In such methods, the laundry detergent composition is diluted to provide a wash liquor having a total surfactant concentration of greater than 300 ppm, preferably from 400 ppm to 2,500 ppm, more preferably from 600 ppm to 1000 ppm. The fabric is then washed in the wash liquor, and preferably rinsed.

The method of the present invention is particularly suited for removing stains, particularly when the stain comprises a combination of mannans and other polysaccharides, and especially when the stains further comprises oils and/or greases such as natural oils and/or natural greases, such as animal fat, vegetable fat, and mixtures thereof.

Methods:

A) pH Measurement:

The pH is measured, at 25° C., using a Santarius PT-10P pH meter with gel-filled probe (such as the Toledo probe, part number 52 000 100), calibrated according to the instructions manual. The pH is measured in a 10% dilution in demineralised water (i.e. 1 part laundry detergent composition and 9 parts demineralised water).

B) Method of Measuring Viscosity:

The viscosity is measured using an AR 2000 rheometer from TA instruments using a cone and plate geometry with a 40 mm diameter and an angle of 10. The viscosity at the different shear rates is measured via a logarithmic shear rate sweep from 0.1 s$^{-1}$ to 1200 s$^{-1}$ in 3 minutes time at 20° C. Low shear viscosity is measured at a continuous shear rate of 0.05 s$^{-1}$.

Examples

The following are examples of liquid laundry detergent compositions of the present invention.

| Active in formula | Ex 1 wt % | Ex 2 wt % | Ex 3 wt % | Ex 4 wt % |
|---|---|---|---|---|
| C12-C15 alkyl ethoxylate sulphate (degree of ethoxylation 2) | 3.2 | 5.7 | 2.6 | 2.8 |
| C12-C14 alkyl ethoxylate (degree of ethoxylation 7) | 4.9 | 13.7 | 3.8 | 4 |
| C11-C13 alkylbenzene sulfonates | 6.2 | 14.4 | 2.5 | 2.5 |
| Coconut Fatty acid | 1.3 | 3 | 0.49 | 0.65 |
| Citric acid | 1.3 | 3.1 | 0.30 | 0.30 |
| 1,2-propanediol | 4.7 | 11.3 | 4 | 4 |
| Monoethanolamine | 2.8 | 6.4 | 2 | 2 |
| Glycerine | 1.2 | 3.2 | 0.51 | 0.67 |
| Polyquaternium 7 | 0 | — | — | 0.1 |
| Protease[1]* | 30 | 30 | 18 | — |
| Amylase[2]* | 10 | 6 | 13 | 8 |
| Cellulase[3]* | 3 | 7 | 13 | 22 |
| Pectate lyase[4]* | 15 | 3 | 7 | 21 |
| Xanthan endoglucanase[5]* | 14 | 7 | 19 | 22 |
| Xanthan lyase[6]* | 6 | 18 | 32 | 5 |
| Mannanase[7]* | 7 | 3 | 10 | 4 |
| Lipase[8]* | 7 | 12 | 15 | 3 |
| HEDP[9] | 0.64 | 1.34 | — | — |
| DTPMP[10] | 0.15 | — | 0.1 | 0.15 |
| PVP-PVI[11] | 0.15 | — | — | 0.1 |
| Brightener | — | 0.12 | 0.06 | — |
| Perfume | 0.5 | 1 | 0.3 | 0.6 |
| Water & minor | Up to 100 | Up to 100 | Up to 100 | Up to 100 |
| pH (using NaOH) | to pH 8 | 8 | 8 | 8 |
| Reco Dose | 50 mls | 50 mls | 50 mls | 50 mls |

*Enzyme levels are given in mg active enzyme protein per 100 g finished product
[1]Lavergy ® Pro 104L, supplied by BASF
[2]Amplify ® 24L, supplied by Novozymes
[3]Biotouch ® FLX1, supplied by AB Enzymes
[4]XPect ® 100L, supplied by Novozymes
[5]Xanthan endoglucanase comprising a polypeptide with at least 60% sequence identity to SEQ ID NO: 1, e.g. the variant of SEQ ID NO: 1 with substitutions at F20P, I302D, S313D, E408D, D476R, Y579W, I602T, S636N, T697G, W719R, V756Y, A824D, N848D, V881Q, T887K, F906A, S928D, A937E, T999R, F1048W.
[6]Xanthan lyase comprising a polypeptide with at least 60% sequence identity to SEQ ID NO: 2, e.g. the variant of SEQ ID NO: 2 with substitutions at E229S, N399K, D458S, K567R, S582K, S635E, N672D, G753E, S754E, A769D, L775A, D777R, D801G, K875T, N892Y.
[7]Mannanase comprising a variant of SEQ ID NO: 4, e.g. the variant of SEQ ID NO: 4 comprising variations at N10T-P19E-G28A-S30T-T38E-S59D-N67D-A68S-N71D-K93R-N97D-Y129M-K143Q-P168S-Q184D-G225C-Y235L-K244L-S258D-N261R-T284E-F297FQ.
[8]Lipase variant of SEQ ID NO: 5, such as Lipex Evity 100 L or 200 L
[9]Hydroxyethylidene Diphosphonic acid
[10]Diethylenetriamine penta(methylene phosphonic acid)
[11]Polyvinylpyrrolidone-polyvinylimidazole, in which the proportion of N-vinylpyrrolidone of at least 50 wt %, having weight average molecular weight of circa 40,000

The following is a low-water liquid laundry detergent composition which can be encapsulated in a water-soluble film in order to provide a water-soluble unit dose article of the present invention. Typically, 24 g of the low-water liquid laundry detergent composition can be encapsulated in polyvinyl alcohol film, in order to provide the water-soluble unit dose article. The enzyme levels are given in mg active enzyme protein per 100 g finished product.

| Active in formula | Ex 5 wt % |
|---|---|
| C14-C15 alkyl ethoxylate (degree of ethoxylation 7) | 3.1 |
| C12-C14 alkyl ethoxylate (degree of ethoxylation 9) | 0.9 |
| C11-C13 alkylbenzene sulfonates | 23.2 |
| C12-C15 alkyl ether sulphate (degree of ethoxylation 2.5) | 15.9 |
| Coconut Fatty acid | 6.4 |
| Citric acid | 0.9 |
| 1,2-propanediol | 12.2 |
| Dipropylene glycol/tripropylene glycol | 4.4 |
| Monoethanolamine | 8.6 |
| Glycerine | 4.1 |
| Protease[1]* | 32 |
| Amylase[2]* | 12 |
| Cellulase[3]* | 5 |
| Pectate lyase[4]* | 13 |
| Xanthan endoglucanase[5]* | 18 |
| Xanthan lyase[6]* | 9 |
| Mannanase[7]* | 10 |
| Lipase[8]* | 11 |
| DTPA (Na salt)[12] | 0.15 |
| Ethoxylated polyethyleneimine[13] | 3.5 |
| Amphiphilic graft polymer[14] | 2.2 |
| Brightener | 0.06 |
| Perfume | 0.5 |
| Water | 9.8 |
| pH (using NaOH) | to pH 8 |
| Balance (perfume, preservative, anti-oxidant, etc) | to 100 |

*Enzyme levels are given in mg active enzyme protein per 100 g finished product
[11]Diethylenetriaminepentaacetic acid, sodium salt
[12]polyethyleneimine branched core having a weight average molecular weight of 600 g/mol, ethoxylated to 20 EO groups per NH, available from BASF
[13]amphiphilic graft polymer based on water-soluble polyethylene oxide (A) as a graft base and side chains formed by polymerization of a vinyl ester component (B), said polymer having an average of ≤1 graft site per 50 alkylene oxide units and weight average molecular weight of from 3000 to 100 000

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A laundry detergent composition comprising:
   a) detersive surfactant, wherein the detersive surfactant comprises a combination of anionic and nonionic surfactant;
   b) an enzyme system comprising:
      i. a xanthan endoglucanase, wherein said xanthan endoglucanase comprises a polypeptide with at least about 60% sequence identity to SEQ ID NO: 1;
      ii. a xanthan lyase, wherein said xanthan lyase comprises a polypeptide with at least about 60% sequence identity to SEQ ID NO: 2, and
      iii. a mannanase, wherein said selected from the group consisting of:
         a) mannanase having mannanase activity and a polypeptide having at least about 85% sequence identity to residues 27-331 of SEQ ID NO: 3, SEQ ID NO: 3 corresponds to the full-length amino acid sequence of the Man7 mannanase endogenous to *Bacillus hemicellulosilyticus* including a signal sequence;
         b) mannanase has mannanase activity and a polypeptide having at least about 60% identity to SEQ ID NO: 4, the mannanase has mannanase activity and a polypeptide having at least 80% identity to SEQ ID NO: 4, wherein SEQ ID NO: 4 corresponds to the full-length amino acid sequence of the Man4 mannanase endogenous to *Paenibacillus sp*;
         c) and mixtures thereof.

2. The laundry detergent composition according to claim 1, wherein the anionic surfactant comprises linear alkyl benzene sulfonate and alkyl alkoxylated sulfate and the ratio of linear alkyl benzene sulfonate surfactant to alkyl alkoxylated sulphate surfactant is from about 0.1 to about 5.

3. The laundry detergent composition according to claim 1, wherein the laundry composition comprises detersive surfactant at a level of from about 1 wt % to about 70 wt %.

4. The laundry detergent composition according to claim 1, wherein the xanthan endoglucanase is a variant with at least 80% sequence identity to SEQ ID NO: 1.

5. The laundry detergent composition according to claim 1, wherein the xanthan endoglucanase has substitutions at one or more of positions selected from: 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 605, 609, 676, 688, 690, 694, 697, 698, 699, 711, 719, 754, 756, 760, 781, 786, 797, 833, 834, 835 and 1048 of SEQ ID NO: 1.

6. The laundry detergent composition according to claim 1, wherein the xanthan endoglucanase has substitutions at one or more of positions selected from S17A, F20P, F20N, F20G, F20Y, K51Q, K51H, E53P, E53G, Y55M, V56M, Y60F, S63F, T87R, A186P, K192N, I320D, I302H, I302V, I302M, H311N, S313D, I387T, K388R, K390Q, I403Y, E408D, E408S, E408P, E408A, E408G, E408N, P410G, Q416S, Q416D, A448E, A448W, A448S, K451S, G471S, S472Y, D476R, Q489P, K507R, K512P, S515V, S538C, Y579W, S598Q, A599S, I602T, I602D, V603P, S605T, G609E, D676H, A688G, Y690F, T694A, T697G, R698W, T699A, T711V, T711Y, W719R, K754R, V756H, V756Y, S760G, T781M, N786K, T797S, A824D, N833D, Q834E, S835D and F1048W.

7. The laundry detergent composition according to claim 1, wherein the xanthan lyase is a variant with at least 80% sequence identity to SEQ ID NO: 2.

8. The laundry detergent composition according to claim 1, wherein the xanthan lyase is a variant with alterations at one or more positions selected from the group consisting of positions: 9, 15, 46, 58, 66, 89, 95, 100, 106, 109, 183, 188, 190, 203, 204, 221, 229, 234, 238, 240, 242, 243, 257, 258, 291, 293, 316, 320, 324, 329, 333, 339, 341, 352, 354, 360, 377, 399, 400, 419, 440, 450, 451, 454, 458, 481, 492, 567, 568, 578, 579, 582, 664, 672, 703, 728, 843, 855, 887, 892, 1008 and 1016 of SEQ ID NO: 2.

9. The laundry detergent composition according to claim 1, wherein the xanthan lyase is a variant with alterations at one or more positions selected from the group consisting of positions: 624, 631, 635, 649, 656, 752, 752, 754, 757, 769, 775, 777, 800, 801, 875, 911, and 915 of SEQ ID NO: 2.

10. The laundry detergent composition according to claim 1, wherein the mannanase has at least about 90% sequence identity to residues 27-331 of SEQ ID NO: 3.

11. The laundry detergent composition according to claim 1, wherein the mannanase is a variant of SEQ ID NO: 3 comprising at least one substitution at positions 123, 158, 180, 272, 285, or 307 or a combination thereof.

12. The laundry detergent composition according to claim 1, wherein the mannanase is a variant of SEQ ID NO: 3 comprising at least one substitution at positions M123, A158, F180, G272, T285, or T307 or a combination thereof.

13. The laundry detergent composition according to claim 1, wherein the mannanase comprises a polypeptide with at least about 85% sequence identity to residues 27-331 of SEQ ID NO: 3.

14. The laundry detergent composition according to claim 1, wherein the mannanase comprises a polypeptide with at least about 60% sequence identity to SEQ ID NO; 4.

15. The laundry detergent composition according to claim 13, wherein the mannanase is a variant of SEQ ID NO: 3 comprising at least one substitution at positions M123, A158, F180, G272, T307, or L316, or a combination thereof.

16. The laundry detergent composition according to claim 14, wherein the mannanase has at least about 80% sequence identity to SEQ ID NO: 4.

17. The laundry detergent composition according to claim 16, wherein the mannanase comprises at least one variation versus SEQ ID NO: 4 selected from:

(a) N10Q/T, P19E/V, S30T, T38E/I/L/M/Q/R/V, S59D/G/K/N/Q/T, L60F/M/V, T62E/I/Q/V, K63L, L66C/T/V, N67A/D/E/G/P/Q/S/V, A68L/M/R/S/W, K70R/V, N71D/H, N74E/C/Q/V, V75I, Q78A/D/L/M, N79E/F/W, K80Q/T, N97E/L/P/Q, V103I, Y129M, T131P, S135A/C/Q, A136E, K143Q/R, F167L/S/W/Y, P168A/E/G/L/M/S/T, Q184D/F/H/L/M/P, N213E, K214C/Q, G225A/C/P/W, T228A/G/H/I/K/S/V/Y, Y235G/I/L/Q/S/V, Q242S/E, K244A/C/G/L/M/P/S, S258A/D/E/G/M/N/P/T, G259A/E/R/S/W, N261I/M/P/Q/R/S/T/V/W/Y, and D283G/H/T; or (b) P19E/V, T38E/I/L/M/Q/R/V, N67A/D/E/G/P/Q/S/V, N97E/L/P/Q, Y129M, K143Q/R, P168A/E/G/L/M/S/T, Q184D/F/H/L/M/P, G225A/C/P/W, T228A/G/H/I/K/S/V/Y, Y235G/I/L/Q/S/V, K244A/C/G/L/M/P/S, S258A/D/E/G/M/N/P/T, and N261I/M/P/Q/R/S/T/V/W/Y; or (c) P19E/V, T38E/I/L/M/Q/R/V, N67A/D/E/G/P/Q/S/V, L85L, Y129M, P168A/E/G/L/M/S/T, Q184D/F/H/L/M/P, G225A/C/P/W, K244A/C/G/L/M/P/S, S258A/D/E/G/M/N/P/T, and N261I/M/P/Q/R/S/T/V/W/Y; or (d) P19E, S30T, T38E, S59V, L60Q, K63R, N67D, N97D, V103I, Y129M, F167Y, P168S, Q184L, G225C, T228V, Y235L, K244L, S258D, and N261R.

18. The laundry detergent composition according to claim 16, wherein the mannanase is a variant of SEQ ID NO: 4 comprising a number of variations to SEQ ID NO:4 selected from: P19E-T38E-N67D-N97D-Y129M-P168S-Q184L-K244L-S258D-N261R; N10T-P19E-G28S-S30T-T38E-N67D-N71D-N97D-Y129M-P168S-Q184L-G225C-Y235L-K244L-S258D-N261R-F297FQ; P19E-S30T-T38E-S59V-L60Q-K63R-N67D-N97D-V103I-Y129M-F167Y-Q184L-G225C-T228V-Y235L-K244L-S258D-N261R-F297FQ; N10T-P19E-S30T-T38E-S59V-L60Q-K63R-N67D-N97D-Y129M-K143Q-P168S-Q184L-G225C-T228V-Y235L-K244L-S258D-N261R-F297FQ; N10T-P19E-S30T-T38E-S59V-L60Q-K63R-N67D-N97D-Y129M-K143Q-P168S-Q184L-G225P-T228V-Y235L-K244L-S258D-N261R-F297FQ; N10T-P19E-S30T-T38E-S59V-L60Q-K63R-N67D-N71D-N97D-V103I-Y129M-K143Q-P168S-Q184L-G225P-T228V-Y235L-K244L-S258D-N261R-F297FQ; A2S-P19E-G28S-S30T-T38E-K63R-N67D-N71D-N74E-K93R-N97D-Y129M-N150T-P168S-Q184L-N213A-G225C-Y235L-K244L-S258D-N261Q-F297FQ; T3R-N10T-P19E-G28A-S30T-T38E-T62E-N67D-N71D-K93R-N97L-E111S-Y129M-D139M-P168S-Q184L-G225C-Y235L-K244L-S258D-N261Q-F297FQ; and N10T-P19E-G28A-S30T-T38E-S59D-N67D-A68S-N71D-K93R-N97D-Y129M-K143Q-P168S-Q184D-G225C-Y235L-K244L-S258D-N261R-T284E-F297FQ.

19. The laundry detergent composition according to claim 1, wherein the enzyme system of the composition further comprises a lipase variant of SEQ ID NO: 5 comprising:

(a) substitution T231R;

(b) substitution N233R or N233C; and (c) at least three further substitutions selected from E1C, D27R, N33Q, G38A, F51V, G91Q, D96E, K98L, K98I, D111A, G163K, H198S, E210Q, Y220F, D254S, I255A, and P256T;

where the positions correspond to the positions of SEQ ID NO: 5 and wherein the lipase variant has at least about 90% but less than about 100% sequence identity to the polypeptide having the amino acid sequence of SEQ ID NO: 5 and wherein the variant has lipase activity.

20. A method of laundering fabric, wherein the method comprises the steps of:

a) providing a laundry detergent composition according to claim 1;

b) diluting the laundry detergent composition to provide a wash liquor having a total surfactant concentration of greater than about 300 ppm; and c) washing fabric in the wash liquor.

* * * * *

SEQUENCE LISTING

```
<160> NUMBER OF SEQ ID NOS: 5

<210> SEQ ID NO 1
<211> LENGTH: 1050
<212> TYPE: PRT
<213> ORGANISM: Paenibacillus sp-62047

<400> SEQUENCE: 1

Ile Ala Gly Val Val Gln Ser Val Asn Val Ser Gln Ala Gly Tyr Ser
1               5                   10                  15

Ser Asn Asp Phe Lys Thr Ala Thr Val Thr Ala Ser Asp Lys Leu Ser
            20                  25                  30

Asp Thr Ser Tyr Gln Ile Leu Gln Gly Thr Thr Val Ile Ala Thr Gly
        35                  40                  45

Thr Met Lys Asp Glu Gly Tyr Val Trp Gly Lys Tyr Val Tyr Ser Ile
    50                  55                  60

Asp Phe Ser Ser Val Thr Ala Thr Gly Thr Asn Phe Thr Ile Arg Ser
65                  70                  75                  80

Asn Gly Val Ser Ser Tyr Thr Phe Pro Ile Gln Thr Asn Met Trp Asn
                85                  90                  95

Glu Tyr Lys Asp Glu Met Thr Ala Phe Tyr Arg Leu Leu Arg Thr Thr
            100                 105                 110

Asp Thr Phe Ala Ala Tyr Pro Ala Gly Tyr Ser Asn Ile Ala Pro Ser
        115                 120                 125

Asn Lys Ile Leu His Pro Asp Ser Phe Leu Asp Asp Ala Phe Ser Pro
    130                 135                 140

Asp Arg Thr Thr His Tyr Asp Leu Thr Gly Gly Trp Phe Asp Ala Gly
145                 150                 155                 160

Asp Tyr Gly Lys Tyr Gly Gly Asn Gln Trp Val Gln Gly Asn Ile Ala
                165                 170                 175

Ile Ser Tyr Leu Arg His Ala Ser Ser Ala Ala Val Asn Phe Asp Lys
            180                 185                 190

Asp Thr Asn Gly Ile Pro Asp Leu Val Asp Glu Ala Ile Phe Gly Ser
        195                 200                 205

Gln Tyr Leu Val Lys Phe Ala Asn Gln Leu Gly Gly Ala Ile His Asn
    210                 215                 220

Ile Leu Arg Lys Gly Gly Phe Val Leu Pro His Lys Val Thr Asp Asn
225                 230                 235                 240

Val Pro Gly Asn Thr Asp Asp Arg Ala Leu Glu Ala Val Glu Ala Val
                245                 250                 255

Gly Gly Ser Gly Lys Ser Ser Gly Ser Leu Ala Ala Thr Ala Arg Ala
            260                 265                 270

Ile Arg Thr Ala Ile Ala Gly Gly Lys Val Ala Ala Asn Lys Val Ala
        275                 280                 285
```

```
Gln Leu Gln Thr Leu Ala Asn Glu Phe Gln Ala Ala Ile Ile Phe
    290                 295                 300
Tyr Asn Tyr Thr Leu Thr His Gln Ser Gly Asn His Gly Ser Tyr Gly
305                 310                 315                 320
Thr Met Asn Asn Gly Gly Ile Ala Asn Pro Leu Leu Trp Ala Glu Val
                325                 330                 335
Gln Leu Tyr Leu Leu Thr Gly Asp Ala Ala Tyr Lys Thr Gln Ala Gln
            340                 345                 350
Thr Arg Ile Asn Ala Ile Asn Glu Ala Tyr Val Ser Thr Asn Tyr
        355                 360                 365
Trp Asp Met His Pro Ile Ala Leu Ala Glu Phe Tyr Pro Val Ala Asp
    370                 375                 380
Ser Ala Ile Lys Thr Lys Ile Gln Ser Ile Leu Lys His Gln Ala Tyr
385                 390                 395                 400
Tyr Phe Ile Thr Leu Met Asp Glu Thr Pro Tyr Gly Val Leu Asn Gln
                405                 410                 415
Phe Gly Asn Phe Gly Val Asn Glu Pro His Ala Ser Tyr Met Ala Asp
            420                 425                 430
Leu Leu Arg Tyr Tyr Glu Leu Phe Asn Asp Pro Val Ala Leu Arg Ala
        435                 440                 445
Ala Lys Lys Ala Leu Tyr Trp Ile Val Gly Asn Asn Pro Trp Asn Ile
    450                 455                 460
Ser Trp Val Ser Gly Val Gly Ser Asn Phe Thr Asp Phe Leu His Thr
465                 470                 475                 480
Arg Leu Asp Glu Glu Ala Tyr Ser Gln Thr Asn Thr Gly Val Val Leu
                485                 490                 495
Pro Gly Ala Met Val Ser Gly Pro Asn Ile Lys Asp Pro Asn Asn Lys
            500                 505                 510
Leu Ser Ser Ser Pro Trp Tyr Glu Asp Lys Pro Ile Trp Ala Asp Asp
        515                 520                 525
Thr Asn Gln Trp Arg Tyr Asn Glu Tyr Ser Val Ser Ile Gln Thr Gly
    530                 535                 540
Leu Phe Tyr Thr Ile Met Gly Leu Ser Ala Leu Gly Gly Asn Ala Ser
545                 550                 555                 560
Thr Gly Gly Ala Glu Pro Val Lys Leu Pro Ile Thr Trp Pro Ile Ile
                565                 570                 575
Gly Asp Tyr Val Thr Gly Asp Val Thr Val Phe Ala Gln Pro Glu Gly
            580                 585                 590
Ser Leu Ser Asn Val Ser Ala Asn Gly Ile Val Leu Ser Pro Ser Asp
        595                 600                 605
Gly Val Tyr Thr Thr Val Ser Thr Ser Ala Asp Ala Pro Tyr Thr
    610                 615                 620
Glu Arg Lys Val Gln Ile Lys Gly Thr Asp Asp Ser Gly Phe Thr Thr
625                 630                 635                 640
Tyr Ser Asn Thr His Phe Thr Val Ala Pro Ala Leu Pro Asp Pro Ser
                645                 650                 655
His Pro Leu Leu Phe Asp Asp Phe Asn Gln Lys Gly Ile Trp Gly Ser
            660                 665                 670
Gln Lys Leu Asp Trp Val Asn Trp Tyr Asn Gln Asn Gly Gly Thr Ala
        675                 680                 685
Ser Tyr Thr Arg Thr Thr Val Asp Thr Arg Thr Val Gly Lys Phe Ala
    690                 695                 700
```

```
His Thr Pro Ala Ala Thr Ser Lys Ala Lys Phe Gln Pro Trp Lys
705                 710                 715                 720

Tyr Asn Ala Asn Leu Asn Gly Tyr Arg Tyr Leu Asn Phe Thr Met Lys
            725                 730                 735

Asn Pro Gly Tyr Pro Asn Thr Lys Ile Arg Ile Ala Ala Asn Asp Gly
        740                 745                 750

Thr Lys Ser Val Asn Leu Thr Ser Gly Glu Val Ala Ile Ser Ser Thr
            755                 760                 765

Trp Thr Thr Tyr Gln Tyr Asp Leu Asn Leu His Pro Thr Leu Asn Lys
        770                 775                 780

Ser Asn Val Leu Ile Glu Val Trp Leu Ser Asn Pro Thr Ala Gly Ala
785                 790                 795                 800

Tyr Gly Glu Ile Leu Ile Asp Glu Ile Ser Ala Val Asn Thr Asn Ser
            805                 810                 815

Gly Thr Ala Pro Thr Leu Ser Ala Thr Gly Val Asn Ala Ser Ile Gly
            820                 825                 830

Asn Gln Ser Thr Val Phe Thr Tyr Thr Ala Thr Tyr Thr Asp Ala Asn
            835                 840                 845

Asn Gln Ala Pro Phe Asp Val Gln Val Val Ile Asp Gly Val Ile Arg
        850                 855                 860

Ser Met Thr Ala Ala Asp Pro Thr Asp Thr Thr Tyr Ser Asp Gly Arg
865                 870                 875                 880

Val Tyr Thr Tyr Ala Thr Thr Leu Pro Val Gly Thr His Lys Phe Tyr
            885                 890                 895

Phe Arg Thr Thr Asp Thr Thr Asn Phe Val Ser Thr Ser Val Gln
        900                 905                 910

Thr Gly Pro Thr Val Ile Arg Asn Lys Leu Glu Ala Glu Val Leu Ser
        915                 920                 925

Ile Asn Leu Thr Asn Tyr Thr His Ala Val Lys Asp Asn Ala Asp Ala
        930                 935                 940

Ser Gly Gly Lys Tyr Arg Leu Phe Asn Gly Arg Gln Ala Asn Asp Tyr
945                 950                 955                 960

Ile Glu Tyr Ala Val Asn Val Pro Lys Ala Gly Thr Tyr Gln Val Ser
            965                 970                 975

Ala Arg Ala Met Arg Leu Ser Asp Asn Gly Ile Tyr Gln Leu Gln Ile
            980                 985                 990

Asn Gly Ser Asn Gln Gly Thr Pro  Phe Asp Thr Tyr Gln Ser Ser Gly
        995                 1000                1005

Lys Tyr Leu Asp Tyr Ala Leu  Gly Asn Val Thr Ile  Thr Ser Pro
    1010                1015                1020

Gly Thr Gln Leu Phe Arg Phe  Lys Val Thr Gly Lys  Asn Ala Ser
    1025                1030                1035

Ser Leu Gly Tyr Lys Leu Pro  Leu Asp Phe Ile Gln
    1040                1045                1050

<210> SEQ ID NO 2
<211> LENGTH: 1037
<212> TYPE: PRT
<213> ORGANISM: Paenibacillus sp.

<400> SEQUENCE: 2

Asp Glu Phe Asp Thr Leu Arg Glu Lys Tyr Lys Ala Met Leu Asn Gly
1               5                   10                  15

Gly Thr Thr Tyr Asn Leu Ser Asp Pro Asp Ile Ala Ala Arg Val Asn
            20                  25                  30
```

```
Ala Ile Thr Val Thr Ala Gln Gly Tyr Trp Asp Ser Met Leu Lys Asp
        35                  40                  45

Pro Asn Arg Asn Arg Leu Trp Asn Asp Ala Pro Phe Gly Ser Asp Ser
    50                  55                  60

Thr Ser Ile Thr Thr Thr Tyr Arg His Leu Tyr Asp Met Ala Leu Ala
65                  70                  75                  80

Tyr Thr Thr Tyr Gly Ser Ser Leu Gln Gly Asn Ala Ala Leu Lys Ala
                85                  90                  95

Asp Ile Ile Ser Gly Leu Asp Trp Met Asn Ala Asn Gln Phe Tyr Asn
            100                 105                 110

Gly Cys Ser Gln Tyr Gln Asn Trp Trp His Trp Gln Ile Gly Gly Pro
            115                 120                 125

Met Ala Leu Asn Asp Ile Val Ala Leu Met Tyr Thr Glu Leu Thr Ala
        130                 135                 140

Thr Gln Ile Ser Asn Tyr Met Ala Ala Ile Tyr Tyr Thr Gln Ala Ser
145                 150                 155                 160

Val Thr Met Thr Gly Ala Asn Arg Leu Trp Glu Ser Gln Val Ile Ala
                165                 170                 175

Ile Ser Gly Ile Leu Asn Lys Asp Ser Ala Arg Val Ala Ala Gly Arg
            180                 185                 190

Asp Gly Ile Ser Ala Leu Leu Pro Tyr Val Ala Lys Gly Asp Gly Phe
            195                 200                 205

Tyr Asn Asp Gly Ser Phe Val Gln His Thr Tyr Tyr Ala Tyr Asn Gly
        210                 215                 220

Gly Tyr Gly Ser Glu Leu Leu Ser Gly Ile Ala Asp Leu Ile Phe Ile
225                 230                 235                 240

Leu Asn Gly Ser Ser Trp Gln Val Thr Asp Pro Asn Lys Asn Asn Val
                245                 250                 255

Tyr Arg Trp Ile Tyr Asp Ser Tyr Glu Pro Phe Ile Tyr Lys Gly Asn
            260                 265                 270

Leu Met Asp Met Val Arg Gly Arg Glu Ile Ser Arg His Gly Leu Gln
        275                 280                 285

Asp Asp Lys Ala Ala Val Thr Val Met Ala Ser Ile Ile Arg Leu Ser
        290                 295                 300

Gln Thr Ala Ala Ser Ala Asp Ala Thr Ala Phe Lys Arg Met Val Lys
305                 310                 315                 320

Tyr Trp Leu Leu Leu Asp Thr Asp Lys Thr Phe Leu Lys Ala Val Ser
                325                 330                 335

Ile Asp Leu Ile Ile Ala Ala Asn Gln Leu Val Asn Asp Ser Thr Val
            340                 345                 350

Thr Ser Arg Gly Glu Leu Val Lys Tyr Lys Gln Phe Ser Gly Met Asp
        355                 360                 365

Arg Ala Val Gln Leu Arg Pro Gly Phe Gly Phe Gly Leu Ser Met Phe
    370                 375                 380

Ser Ser Arg Ile Gly Asn Tyr Glu Ser Ile Asn Ala Glu Asn Lys
385                 390                 395                 400

Gly Trp His Thr Gly Asp Gly Met Thr Tyr Leu Tyr Asn Thr Asp Leu
                405                 410                 415

Ser Gln Phe Asn Asp His Phe Trp Ala Thr Val Asp Asn Tyr Arg Leu
            420                 425                 430

Pro Gly Thr Thr Val Leu Gln Asn Thr Gln Thr Ala Asn Ser Arg
        435                 440                 445
```

```
Ser Asp Lys Ser Trp Ala Gly Gly Thr Asp Ile Leu Gly Gln Tyr Gly
450                 455                 460

Val Ser Gly Met Glu Leu His Thr Val Gly Lys Ser Leu Thr Ala Lys
465                 470                 475                 480

Lys Ser Trp Phe Met Phe Asp Asp Glu Ile Val Ala Leu Gly Ser Gly
                485                 490                 495

Ile Ala Ser Thr Asp Gly Ile Ala Thr Glu Thr Ile Val Glu Asn Arg
                500                 505                 510

Lys Leu Asn Ser Ser Gly Asn Asn Ala Leu Ile Val Asn Gly Thr Ala
                515                 520                 525

Lys Pro Gly Ser Leu Gly Trp Ser Glu Thr Met Thr Gly Thr Asn Tyr
530                 535                 540

Ile His Leu Ala Gly Ser Val Pro Gly Ser Asp Ile Gly Tyr Tyr Phe
545                 550                 555                 560

Pro Gly Gly Ala Ala Val Lys Gly Leu Arg Glu Ala Arg Ser Gly Ser
                565                 570                 575

Trp Ser Ser Leu Asn Ser Ser Ala Ser Trp Lys Asp Ser Thr Leu His
                580                 585                 590

Thr Arg Asn Phe Met Thr Leu Trp Phe Asp His Gly Met Asn Pro Thr
            595                 600                 605

Asn Gly Ser Tyr Ser Tyr Val Leu Leu Pro Asn Lys Thr Ser Ser Ala
            610                 615                 620

Val Ala Ser Tyr Ala Ala Thr Pro Gln Ile Ser Ile Leu Glu Asn Ser
625                 630                 635                 640

Ser Ser Ala Gln Ala Val Lys Glu Thr Gln Leu Asn Val Thr Gly Ile
                645                 650                 655

Asn Phe Trp Asn Asp Glu Pro Thr Thr Val Gly Leu Val Thr Ser Asn
                660                 665                 670

Arg Lys Ala Ser Val Met Thr Lys Glu Thr Ala Ser Asp Phe Glu Ile
                675                 680                 685

Ser Val Ser Asp Pro Thr Gln Ser Asn Val Gly Thr Ile Tyr Ile Asp
                690                 695                 700

Val Asn Lys Ser Ala Thr Gly Leu Ile Ser Lys Asp Asn Glu Ile Thr
705                 710                 715                 720

Val Ile Gln Tyr Tyr Pro Thr Met Lys Phe Lys Val Asn Val Asn Asn
                725                 730                 735

Ser Gly Gly Lys Ser Tyr Lys Val Lys Phe Ser Leu Thr Gly Thr Pro
                740                 745                 750

Gly Ser Asn Pro Ser Pro Ile Pro Ile Pro Asn Pro Tyr Glu Ala Glu
                755                 760                 765

Ala Leu Pro Ile Asn Ala Leu Thr Asp Thr Pro Val Val Tyr Asn Asp
770                 775                 780

Ala Asn Ala Ser Gly Gly Lys Lys Leu Gly Phe Asn Asn Ala Val
785                 790                 795                 800

Asp Asp Tyr Val Glu Phe Ser Leu Asp Val Thr Gln Pro Gly Thr Tyr
                805                 810                 815

Asp Val Lys Ser Arg Ile Met Lys Ser Thr Asn Ser Gly Ile Tyr Gln
                820                 825                 830

Leu Ser Ile Asn Gly Thr Asn Val Gly Ser Ala Gln Asp Met Phe Trp
                835                 840                 845

Thr Thr Ser Glu Leu Ser Lys Glu Phe Thr Met Gly Ser Tyr Ser Phe
850                 855                 860

Ser Thr Pro Gly Ser Tyr Leu Phe Arg Leu Lys Thr Thr Gly Lys Asn
```

```
            865                 870                 875                 880
Val Ser Ser Ser Gly Tyr Lys Leu Met Leu Asp Asn Phe Ser Leu Val
                    885                 890                 895

Ser Thr Gly Ile Asp Thr Thr Val Ile Val Asp Asn Ala Asp Ala Ala
                    900                 905                 910

Gly Val Thr Lys Val Gly Thr Trp Thr Gly Thr Asn Thr Gln Thr Asp
                    915                 920                 925

Arg Tyr Gly Ala Asp Tyr Ile His Asp Gly Asn Thr Gly Lys Gly Thr
                    930                 935                 940

Lys Ser Val Thr Phe Thr Pro Asn Val Pro Ile Ser Gly Thr Tyr Gln
945                 950                 955                 960

Val Tyr Met Met Trp Ala Ala His Thr Asn Arg Ala Thr Asn Val Pro
                    965                 970                 975

Val Asp Val Thr His Ser Gly Thr Ala Thr Leu Asn Val Asn Gln
                    980                 985                 990

Gln Gly Asn Gly Gly Val Trp Asn Leu Leu Gly Thr Tyr Ser Phe Asn
                    995                 1000                1005

Ala Gly Ser Thr Gly Ala Ile Lys Ile Arg Thr Asp Ala Thr Asn
    1010                1015                1020

Gly Tyr Val Val Ala Asp Ala Val Lys Leu Val Lys Val Pro
    1025                1030                1035

<210> SEQ ID NO 3
<211> LENGTH: 490
<212> TYPE: PRT
<213> ORGANISM: Bacillus hemicellulosilyticus

<400> SEQUENCE: 3

Met Arg Asn Phe Gly Lys Leu Ile Val Ser Ser Cys Leu Leu Phe Ser
1               5                   10                  15

Phe Phe Leu Phe Ala Ser Asp Gly His Ser Gln Thr His Ser Gly Phe
                20                  25                  30

Tyr Ile Glu Gly Ser Thr Leu Tyr Asp Ala Asn Gly Glu Pro Phe Val
            35                  40                  45

Met Arg Gly Ile Asn His Gly His Ala Trp Tyr Lys His Asp Ser Asn
        50                  55                  60

Val Ala Ile Pro Ala Ile Ala Asn Gln Gly Ala Asn Thr Ile Arg Ile
65                  70                  75                  80

Val Leu Ser Asp Gly Gly Gln Trp Ala Lys Asp Ile Asn Thr Leu
                85                  90                  95

Asn Gln Val Leu Asp Leu Ala Glu Glu His Glu Met Ile Ala Val Val
                100                 105                 110

Glu Val His Asp Ala Thr Gly Ser Asn Ser Met Ala Asp Leu Asn Arg
                115                 120                 125

Ala Val Asp Tyr Trp Ile Glu Met Lys Asp Ala Leu Ile Gly Lys Glu
        130                 135                 140

Asp Arg Val Ile Ile Asn Ile Ala Asn Glu Trp Tyr Gly Ala Trp Asp
145                 150                 155                 160

Gly Gln Gly Trp Ala Asn Gly Tyr Lys Glu Val Ile Pro Arg Leu Arg
                165                 170                 175

Asn Ala Gly Phe Thr His Thr Leu Met Val Asp Ala Ala Gly Trp Gly
                180                 185                 190

Gln Tyr Pro Gln Ser Ile His Asp Tyr Gly Gln Glu Val Phe Asn Ala
        195                 200                 205
```

```
Asp Pro Leu Ala Asn Thr Met Phe Ser Ile His Met Tyr Glu Tyr Ala
    210                 215                 220

Gly Gly Asn Ala Ser Met Val Gln Ser Asn Ile Asp Gly Val Val Asp
225                 230                 235                 240

Gln Gly Leu Ala Leu Val Ile Gly Glu Phe Gly His Met His Thr Asp
                245                 250                 255

Gly Asp Val Asp Glu Ala Thr Ile Leu Ser Tyr Ser Gln Gln Arg Gly
            260                 265                 270

Val Gly Trp Leu Ala Trp Ser Trp Lys Gly Asn Gly Thr Gln Trp Glu
        275                 280                 285

Tyr Leu Asp Leu Ser Tyr Asp Trp Gln Gly Thr Asn Leu Thr Ser Trp
    290                 295                 300

Gly Asn Thr Ile Val His Gly Pro Asn Gly Leu Leu Glu Thr Ser Ile
305                 310                 315                 320

Pro Ser Ser Ile Phe His Thr Ala Pro Asn Asn Gly Asp Pro Pro Pro
                325                 330                 335

His Asn Gly Asn Glu Thr Ile Leu Tyr Asp Phe Glu His Gly Thr Gln
            340                 345                 350

Gly Trp Ser Gly Ser Ser Leu Leu Gly Gly Pro Trp Thr Thr Asn Glu
        355                 360                 365

Trp Ser Thr Asn Gly Asn His Ser Leu Lys Ala Asp Ile Phe Leu Ser
    370                 375                 380

Ala Asn Ser Lys His Glu Leu Ala Lys Val Glu Asn Arg Asn Leu Ser
385                 390                 395                 400

Gly Tyr Ser Thr Leu Gln Ala Thr Val Arg His Ala His Trp Gly Asn
                405                 410                 415

Val Gly Asn Leu Thr Ala Arg Met Tyr Val Lys Thr Gly Ser Asn Tyr
            420                 425                 430

Ser Trp Phe Asn Gly Asp Pro Ile Pro Val Asn Ser Ala Asn Gly Thr
        435                 440                 445

Thr Val Thr Leu Pro Leu Ser Ser Ile Pro Asn Leu Asn Asp Val Lys
    450                 455                 460

Glu Ile Gly Val Glu Phe Ile Gly Ala Ser Asn Ser Asn Gly Gln Thr
465                 470                 475                 480

Ala Ile Tyr Leu Asp His Val Thr Ile Gln
                485                 490

<210> SEQ ID NO 4
<211> LENGTH: 297
<212> TYPE: PRT
<213> ORGANISM: Paenibacillus sp.

<400> SEQUENCE: 4

Met Ala Thr Gly Phe Tyr Val Ser Gly Asn Lys Leu Tyr Asp Ser Thr
1               5                   10                  15

Gly Lys Pro Phe Val Met Arg Gly Val Asn His Gly His Ser Trp Phe
            20                  25                  30

Lys Asn Asp Leu Asn Thr Ala Ile Pro Ala Ile Ala Lys Thr Gly Ala
        35                  40                  45

Asn Thr Val Arg Ile Val Leu Ser Asn Gly Ser Leu Tyr Thr Lys Asp
    50                  55                  60

Asp Leu Asn Ala Val Lys Asn Ile Ile Asn Val Val Asn Gln Asn Lys
65                  70                  75                  80

Met Ile Ala Val Leu Glu Val His Asp Ala Thr Gly Lys Asp Asp Tyr
                85                  90                  95
```

```
Asn Ser Leu Asp Ala Ala Val Asn Tyr Trp Ile Ser Ile Lys Glu Ala
            100                 105                 110

Leu Ile Gly Lys Glu Asp Arg Val Ile Val Asn Ile Ala Asn Glu Trp
        115                 120                 125

Tyr Gly Thr Trp Asn Gly Ser Ala Trp Ala Asp Gly Tyr Lys Lys Ala
    130                 135                 140

Ile Pro Lys Leu Arg Asn Ala Gly Ile Lys Asn Thr Leu Ile Val Asp
145                 150                 155                 160

Ala Ala Gly Trp Gly Gln Phe Pro Gln Ser Ile Val Asp Tyr Gly Gln
                165                 170                 175

Ser Val Phe Ala Ala Asp Ser Gln Lys Asn Thr Val Phe Ser Ile His
            180                 185                 190

Met Tyr Glu Tyr Ala Gly Lys Asp Ala Ala Thr Val Lys Ala Asn Met
        195                 200                 205

Glu Asn Val Leu Asn Lys Gly Leu Ala Leu Ile Ile Gly Glu Phe Gly
    210                 215                 220

Gly Tyr His Thr Asn Gly Asp Val Asp Glu Tyr Ala Ile Met Arg Tyr
225                 230                 235                 240

Gly Gln Glu Lys Gly Val Gly Trp Leu Ala Trp Ser Trp Tyr Gly Asn
                245                 250                 255

Ser Ser Gly Leu Asn Tyr Leu Asp Met Ala Thr Gly Pro Asn Gly Ser
            260                 265                 270

Leu Thr Ser Phe Gly Asn Thr Val Val Asn Asp Thr Tyr Gly Ile Lys
        275                 280                 285

Asn Thr Ser Gln Lys Ala Gly Ile Phe
    290                 295

<210> SEQ ID NO 5
<211> LENGTH: 269
<212> TYPE: PRT
<213> ORGANISM: Thermomyces lanuginosus

<400> SEQUENCE: 5

Glu Val Ser Gln Asp Leu Phe Asn Gln Phe Asn Leu Phe Ala Gln Tyr
1               5                   10                  15

Ser Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
```

-continued

```
                165                 170                 175
Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
                260                 265
```